United States Patent [19]
Fleming et al.

[11] Patent Number: 5,349,079
[45] Date of Patent: Sep. 20, 1994

[54] PROCESS FOR FORMING α-AMINONITRILES FROM CARBONYL COMPOUND AND FATTY AMINE HYDROHALIDE

[75] Inventors: Alison A. Fleming, Mohegan Lake; Meiylin F. Antezzo, Carmel, both of N.Y.

[73] Assignee: Akzo Nobel nv, Arnhem, Netherlands

[21] Appl. No.: 136,489

[22] Filed: Oct. 13, 1993

Related U.S. Application Data

[63] Continuation of Ser. No. 989,618, Dec. 14, 1992, abandoned.

[51] Int. Cl.⁵ ............................................ C07C 253/30
[52] U.S. Cl. ................................................... 558/346
[58] Field of Search ........................................ 558/346

[56] References Cited

U.S. PATENT DOCUMENTS 2,164,781  7/1939  Platz et al. .................... 552/443 X
4,551,526  11/1985  Mai et al. ..................... 558/372 X

FOREIGN PATENT DOCUMENTS 60-94122  7/1975  Japan.

OTHER PUBLICATIONS

Stout, et al., J. Org. Chem. (1983), 48, pp. 5369–5373.
Matier, et al., J. Med. Chem. (1973), 16, pp. 901–908.
Mai, et al., Synthetic Communications 15(2), (1985), pp. 157–163.
The Merck Index, 10th Ed., (1983), p. ONR-87.
Shafran, et al., "Synthesis & Properties of α-Aminonitriles", Russian Chemical Reviews 58(2), (1989), pp. 148–162.

*Primary Examiner*—Joseph Paul Brust
*Attorney, Agent, or Firm*—Richard P. Fennelly; Louis A. Morris

[57] ABSTRACT

α-aminonitrile compounds can be synthesized by reacting a carbonyl compound, for example an aldehyde, such as, one containing an alkyl group, with a fatty amine hydrohalide, for example, a fatty amine hydrochloride, in the presence of a cyanide source, for example, an alkali metal cyanide.

12 Claims, No Drawings

PROCESS FOR FORMING α-AMINONITRILES FROM CARBONYL COMPOUND AND FATTY AMINE HYDROHALIDE

This application is a continuation of U.S. Ser. No. 07/989,618, filed Dec. 14, 1992, now abandoned.

BACKGROUND OF THE INVENTION

It is known to synthesize α-aminonitriles by reaction of an aldehyde, an amine, and a cyanide source. Some representative prior art references which illustrate the use of amines in such a synthesis include the following: U.S. Pat. No. 4,551,526; Japanese Patent Publication No. 75/94,122; U.S. Pat. No. 2,164,781; and German Offenlegungsschrift No. 2,442,239.

A modification of the Strecker amino acid synthesis, which reacted aldehydes with ammonia and hydrogen cyanide followed by hydrolysis, is the Zelinsky-Stadnikoff modification which uses ammonium chloride and potassium cyanide, as alternative reagents, with the aldehyde of interest.

D. M. Stout et al., Journal of Organic Chemistry, 1983, 48, 5369–5373 discuss an asymmetric Strecker synthesis in which an aldehyde, sodium cyanide, and (R)- and (S)-α-methyl-benzylamine hydrochlorides are reacted to form chiral aminonitriles.

W. L. Matier et al., Journal of Medicinal Chemistry, 1973, Vol. 16, No. 8, 901–908 discuss the use of benzylamine hydrochloride, rather than ammonium chloride, in a Strecker reaction to produce high yields of α-benzylaminophenylacetonitriles.

DESCRIPTION OF THE INVENTION

The present invention relates to the synthesis of α-aminonitrile compounds by reacting a carbonyl compound, such as an aldehyde which contains an alkyl group, with a fatty amine hydrohalide, for example, a fatty amine hydrochloride, in the presence of a cyanide source, for example, an alkali metal cyanide. This method avoids the necessity of using a reagent such as sodium bisulfite to form the bisulfite adducts of the selected aldehyde which can be both time consuming and difficult to practice with certain aldehydes.

The term "carbonyl compound" as used herein to describe one of the essential reagents for use with the present invention is to be construed as covering carbonyl compounds which are not derivatives of carboxylic acids but which, rather, have one or more hydrocarbyl groups directly bonded to the carbonyl radical, C=O. Both ketones (R-C(O)R') and aldehydes (R-C(O)H) are intended to be covered with R and R' being the same or different and selected from alkyl, aryl, alkylaryl, arylalkyl, and the like. Polyhydroxy substituted carbohydrate materials, such as the aldoses and ketoses are also intended to be covered herein. The aldehyde which may be used in the present process has the formula RC(O)H, with R being either straight chain or branched chain alkyl of from one to about fourteen carbon atoms.

The fatty amine hydrohalide reagent which is used herein can be selected from the primary and secondary amine hydrohalides with the hydrochlorides being preferred. The primary amines will have the fatty alkyl group (preferably of ten to twenty-two carbon atoms in length) as the sole organo-substituent, whereas the secondary amine will contain a second organo-substituent, preferably alkyl of from about one to about twenty-two carbon atoms. The fatty amine hydrohalide reagent can also be a fatty alkyl alkylene diamine of the preferred formula R'NHR"NH(R'''), where R' is fatty alkyl as defined above, R" is an alkylene group, preferably of from one to six carbon atoms, and R''' can be either hydrogen or alkyl of from one to twenty-two carbon atoms.

The cyanide source is preferably an alkali metal cyanide such as sodium cyanide although other known cyanide sources can also be employed. This type of preferred cyanide source avoids the need for a more expensive source such as trimethylsilylcyanide and also avoids the handling of hydrogen cyanide.

The solvent which can be used can either be an organic solvent, a mixed organic/aqueous solvent, or an all aqueous solvent. The organic solvent, if used either alone or in combination with water, can be selected from the water miscible polar protic solvents, such as alcohols, or the water miscible polar aprotic solvents, such as tetrahydrofuran or dimethylsulfoxide. Polar and non-polar solvents which are immiscible with water, such as methylene chloride or toluene, can also be employed. The temperature can range widely, e.g., from about 0° C. up to the reflux temperature of the solvent with temperatures of from about room temperature (about 20° C.) to about 60° C. being preferred. Stoichiometric amounts of the amine hydrochloride and carbonyl compound reagents are preferably used since use of an excess of either reagent will result in unreacted material or side products. The reaction is run at moderately basic pH values (e.g., pH values of about 10 or so). The use of strong base (e.g., sodium hydroxide) will encourage imine, rather than α-aminonitrile, formation, and should not be employed in any amount which would give such a result. Weaker bases, such as ammonium hydroxide, may be used.

The process of the invention can, for example, be readily practiced by first dissolving the selected aldehyde in a suitable solvent such as a mixture of water and an alkyl alkanol such as isopropyl alcohol (e.g., in a 4:1 ratio) at an appropriate temperature which can be room temperature. The selected amine hydrohalide reagent is then added to the solution, followed by the cyanide source. The amine hydrohalide unexpectedly need not be soluble in the reaction medium. An appropriate base, ammonium hydroxide being preferred, can be used to keep the reaction moderately alkaline. Stirring of the reaction mixture at room temperature causes production of the product which can be separated as a liquid or solid from the aqueous layer, washed with water, and dried.

The products of the present invention exhibit surfactant properties when placed in mixed aqueous-organic systems. They are also known bactericidal/fungicidal compounds (see Japanese Patent Publication No. 94122/1975).

The present invention is further illustrated by the Examples which follow.

EXAMPLES 1–6

These Examples illustrate the synthesis of aminonitrile derivatives of certain fatty amines via the hydrochloride salt of the amine without the need to use sodium bisulfite to form the bisulfite adduct of the aldehyde.

The general procedure that was employed first dissolved the selected aldehyde in a 4:1 (w/w) mixture of water and isopropyl alcohol at room temperature.

Water may be used as the sole solvent, if desired. The selected amine hydrohalide was then added followed immediately by sodium cyanide. Ammonium hydroxide can be used to make the reaction more alkaline. Stirring was continued at room temperature. The product separated out as a liquid or solid from the aqueous layer, was washed with water, and then dried.

Table 1 set forth below shows the yields and product distributions (the latter being determined by quantitative $^{13}C$ NMR) for various selected amine hydrochloride and aldehyde reagents:

TABLE 1

| Amine Hydrochloride | Aldehyde | Yield | Product Distribution |
|---|---|---|---|
| Dodecylamine | isobutyraldehyde | 98%[a] | 98% aminonitrile, 2% amine |
| Dodecylamine | isobutyraldehyde | 98%[b] | 95% aminonitrile, 5% amine |
| Dodecylamine | 2-ethylhexanal | 99%[a] | >99% aminonitrile, no amine |
| Dodecylamine | 2-ethylhexanal | 98%[b] | 95% aminonitrile, 5% amine |
| ARMEEN T | isobutyraldehyde | 83%[a] | 96.6% aminonitrile, 3.4% cyanohydrin |
| ARMEEN T | 2-ethylhexanal | 93%[a] | 90.9% aminonitrile, 6.4% cyanohydrin, 2.7% imine |

*ARMEEN T = a trademark of Akzo Chemicals Inc. for tallow alkyl amine containing a minimum of 97% primary amine having a minimum amide number of 208.
[a] no NH₄OH.
[b] 1.0 equivalents of NH₄OH added.

EXAMPLES 7-11

These Examples illustrate a series of reactions, using the general procedure of Examples 1-6 in an entirely aqueous reaction medium with no isopropanol, in which certain reaction conditions were altered as described below in Table 2:

TABLE 2

| Amine Hydrochloride | Aldehyde | Conditions* | Yield and Product Distribution |
|---|---|---|---|
| Dodecylamine | 2-ethylhexanal | No HN₄OH, RT, 3 hrs | 89.5%: 95.5% α-aminonitrile; 4% imine; 0.5% aldehyde |
| Dodecylamine | 2-ethylhexanal | NH₄OH, RT, 3 hrs | 89.4%: 10% imine |
| Dodecylamine | isobutyraldehyde | NH₄OH, RT | 87.2%: 10% imine |
| Dodecylamine | isobutyraldehyde | No NH₄OH, RT | 90.2%: 94.9% α-aminonitrile; 2.6% imine; 0.6% aldehyde; 1.9% unknown |
| Dodecylamine | 2-ethylhexanal | NaOH, RT (0.8 eq., pH = 11) | 100%: all imine |
| Dodecylamine | isobutyraldehyde | NaOH, RT (0.8 eq., pH = 11) | 80%: all imine |
| ARMEEN 18D** | 2-ethylhexanal | No NH₄OH, RT, 3 hrs | 80%: all imine 83%: 95.8% α-aminonitrile; 4.2% imine |
| ARMEEN 18D | isobutyraldehyde | No NH₄OH, RT, 3 hrs | 96%: 96.6% α-aminonitrile; 3.4% imine |
| ARMEEN T | 2-ethylhexanal | No NH₄OH, RT, 3 hrs | 100%: 97.9% α-aminonitrile; 2.1% imine |
| ARMEEN T | isobutyraldehyde | No NH₄OH, RT, 3 hrs | 91%: 97.3% α-aminonitrile: 2.7% imine |

*RT = room temperature.
**ARMEEN 18D is a trademark of Akzo Chemicals Inc. for octyldecylamine containing 99% primary amine.

The above illustrate that the addition of strong base (sodium hydroxide) to yield a pH of 11, which occurred immediately before potassium cyanide addition, caused production of all imine and no α-aminonitrile product, whereas the use of a weaker base, such as ammonium hydroxide which gave a pH of 9, successfully resulted in α-aminonitrile production.

COMPARATIVE EXAMPLES 13-16

These Examples further illustrate the reaction of various amines, rather than their hydrochlorides, with isobutyraldehyde and sodium bisulfite in an aqueous reaction medium without organic solvent. The same general procedure used in Examples 1-6 was employed with this modification to the solvent medium except the aldehyde and bisulfite were allowed to react at room temperature prior to addition of the amine and cyanide:

TABLE 3

| Amine | Yield | Product Distribution |
|---|---|---|
| Dodecylamine | 93% | 93.7% α-aminonitrile 5.8% amine 0.5% imine |
| Tetradecylamine | 99% | 89.2% α-aminonitrile 10.2% amine 0.6% imine |
| ARMEEN 18D* | 80% | >98% α-aminonitrile |
| ARMEEN T | 89% | 94.8% α-aminonitrile 4% amine 1.2% imine |

The above data indicate that the selected amines and aldehydes, such as isobutyraldehyde, react well in aqueous solution.

COMPARATIVE EXAMPLES 17-21

These Examples are analogous to Comparative Examples 13-16 but utilize a higher molecular weight aldehyde reagent, namely, 2-ethylhexanal and illustrate that when such an aldehyde is selected, the reaction can become unreliable:

TABLE 4

| Amine | Yield | Product Distribution |
|---|---|---|
| Tetradecylamine | 77% | 50% α-aminonitrile 50% amine |
| ARMEEN 18D | 95% | >99% α-aminonitrile |
| ARMEEN TD* | 90% | 92% α-aminonitrile 8% amine |
| ARMEEN TD | 90% | 40% α-aminonitrile 60% amine |
| ARMEEN TD** | 78% | 66% α-aminonitrile |

TABLE 4-continued

| Amine | Yield | Product Distribution |
|-------|-------|----------------------|
|       |       | 33% amine            |

*ARMEEN TD is a trademark of Akzo Chemicals Inc. for tallow alkyl amine having a minimum primary amine content of 98% and a minimum amine number of 210.
**ammonium hydroxide was added to the reaction medium.

The collective import of Comparative Examples 13-21 is that use of an amine reagent, as contrasted to use of an amine hydrochloride reagent, with an aldehyde, in an all aqueous, sodium bisulfite-sodium cyanide procedure for the synthesis of α-aminonitriles, can lead to unreliable results (e.g., poor conversion to α-aminonitrile) especially if higher molecular weight aldehydes are selected.

EXAMPLES 22-24

These Examples illustrate practice of the present invention using dodecylamine hydrochloride with the ketones identified below. The procedure used in Examples 1-6 was employed.

| Ketone | Yield | Product Distribution |
|--------|-------|----------------------|
| Acetone | 80% | 88.3% aminonitrile |
|  |  | 2.5% imine |
|  |  | 8.6% amine |
|  |  | 0.6% ketone |
| Cyclohexanone | 75% | 98.2% aminonitrile |
|  |  | 1.8% amine |
| Methyl ethyl ketone | 90% | 90% aminonitrile |
|  |  | 2.3% imine |
|  |  | 6.9% amine |
|  |  | 0.8% ketone |

The foregoing Examples, since they are presented to merely illustrate certain embodiments of the present invention, should not be construed in a limiting sense.

The scope of protection sought is set forth in the claims which follow.

I claim:

1. A process for forming an α-aminonitrile compound which comprises reacting a carbonyl compound selected from the group consisting of an aldehyde and a ketone with a fatty amine hydrohalide reagent, comprising a fatty alkyl group of from ten to twenty-two carbon atoms, selected from the group consisting of a primary amine hydrohalide, a secondary amine hydrohalide, and a fatty alkyl alkylene diamine of the formula R'NHR"NH(R'''), where R' is fatty alkyl of from ten to twenty-two carbon atoms, R" is alkylene of from one to six carbon atoms, and R''' is hydrogen or alkyl of from one to twenty-two carbon atoms in the presence of a cyanide source to form said α-aminonitrile compound.

2. A process as claimed in claim 1 wherein the fatty amine hydrohalide is a fatty amine hydrochloride.

3. A process as claimed in claim 1 wherein the carbonyl compound is an aldehyde.

4. A process as claimed in claim 2 wherein the carbonyl compound is an aldehyde.

5. A process as claimed in claim 1 wherein the cyanide source is an alkali metal cyanide.

6. A process as claimed in claim 2 wherein the cyanide source is an alkali metal cyanide.

7. A process as claimed in claim 3 wherein the cyanide source is an alkali metal cyanide.

8. A process as claimed in claim 4 wherein the cyanide source is an alkali metal cyanide.

9. A process as claimed in claim 1 wherein the carbonyl compound is a ketone.

10. A process as claimed in claim 2 wherein the carbonyl compound is a ketone.

11. A process as claimed in claim 10 wherein the cyanide source is an alkali metal cyanide.

12. A process as claimed in claim 11 wherein the cyanide source is an alkali metal cyanide.

* * * * *